United States Patent [19]

Birchak et al.

[11] Patent Number: 5,741,962
[45] Date of Patent: Apr. 21, 1998

[54] APPARATUS AND METHOD FOR ANALYZING A RETRIEVING FORMATION FLUID UTILIZING ACOUSTIC MEASUREMENTS

[75] Inventors: James R. Birchak, Spring; Mark A. Proett, Houston, both of Tex.

[73] Assignee: Halliburton Energy Services, Inc., Houston, Tex.

[21] Appl. No.: 628,408

[22] Filed: Apr. 5, 1996

[51] Int. Cl.[6] .......................... E21B 47/10; E21B 43/00; G01V 1/40
[52] U.S. Cl. .................. 73/152.16; 73/152.17; 73/152.28; 73/597; 73/599
[58] Field of Search .................. 73/152.16, 152.17, 73/152.01, 152.28, 152.38, 152.47, 152.58, 152.26, 597, 599, 629; 166/250, 264, 100; 175/40, 48, 50

[56] References Cited

U.S. PATENT DOCUMENTS

| | | |
|---|---|---|
| 2,563,284 | 8/1951 | Seay, Jr. ............................ 166/1 |
| 2,681,110 | 6/1954 | Harrison ........................... 166/55 |
| 2,776,013 | 1/1957 | Tausch .............................. 166/150 |
| 2,982,130 | 5/1961 | McMahan ........................ 73/155 |
| 3,009,518 | 11/1961 | Taylor et al. ................... 166/100 |
| 3,010,517 | 11/1961 | Lanmon, II ..................... 166/100 |
| 3,011,554 | 12/1961 | Desbrandes et al. ........... 166/100 |
| 3,012,611 | 12/1961 | Haines .............................. 166/147 |
| 3,022,826 | 2/1962 | Kisling, III ...................... 166/100 |
| 3,035,440 | 4/1962 | Reed ................................. 73/151 |
| 3,055,764 | 9/1962 | Pryor et al. ...................... 166/109 |
| 3,075,585 | 1/1963 | Carlton et al. ................... 166/164 |
| 3,079,793 | 3/1963 | Le Bus et al. ................... 73/152 |
| 3,121,459 | 2/1964 | Van Ness, Jr. et al. ........ 166/3 |
| 3,127,933 | 4/1964 | Graham et al. ................. 166/3 |
| 3,134,441 | 5/1964 | Barry et al. ..................... 166/187 |
| 3,177,938 | 4/1965 | Roussin ............................ 166/4 |
| 3,190,360 | 6/1965 | Farley .............................. 166/226 |
| 3,207,223 | 9/1965 | Hugel .............................. 166/163 |
| 3,209,835 | 10/1965 | Bourne, Jr. et al. ............ 166/187 |
| 3,217,804 | 11/1965 | Peter ................................. 166/63 |
| 3,217,806 | 11/1965 | Voetter ............................. 166/163 |
| 3,248,938 | 5/1966 | Hill et al. ......................... 73/155 |
| 3,253,654 | 5/1966 | Briggs, Jr. et al. ............. 166/100 |

(List continued on next page.)

FOREIGN PATENT DOCUMENTS

| | | | |
|---|---|---|---|
| 2172630 | 9/1986 | United Kingdom | E21B 49/08 |
| 2172631 | 9/1986 | United Kingdom | E21B 49/08 |

OTHER PUBLICATIONS

M.C. Waid, M.A. Proett, C.C. Chen, & W.T. Ford, Improved Models for Interpreting the Pressure Response of Formation Testers, Society of Petroleum Engineers, Dallas, Texas, Oct. 6–9, 1991, pp. 889–904.

Primary Examiner—Hezron E. Williams
Assistant Examiner—J. David Wiggins
Attorney, Agent, or Firm—Madan & Morris, PLLC

[57] ABSTRACT

This invention provides a closed-loop system for in situ testing of formation fluid conditions and for selectively collecting substantially mud filtrate free formation fluid samples at original formation conditions. The system contains an elongated member having a probe that is sealingly placed against the wellbore formation to withdraw formation fluids. A surface controlled pump controls the flow of a fluid from the formation into a flowline placed in the elongated member. A pressure sensor provides downhole hydrostatic pressure and an acoustic density cell provides the speed of sound in the fluid, acoustic impedance of the fluid and acoustic absorption coefficient of the fluid in the flowline. The system determines the density and compressibility of the formation fluid in the flowline from the speed of sound in the fluid and acoustic impedance of the fluid. The formation of the bubbles are identified or detected from the acoustic absorption coefficient of the fluid in the flowline. The system controls the movement of fluid into the flowline to selectively collect the formation fluid samples that are substantially free from any mud filtrates while maintaining the fluid pressure above the bubble point pressure of the formation fluid. This invention provides a method for retrieving and collecting formation fluids from a zone of interest in a wellbore at the original formation conditions.

26 Claims, 6 Drawing Sheets

U.S. PATENT DOCUMENTS

| | | | |
|---|---|---|---|
| 3,254,531 | 6/1966 | Briggs, Jr. | 73/155 |
| 3,254,710 | 6/1966 | Jensen | 166/3 |
| 3,261,402 | 7/1966 | Whitten | 166/63 |
| 3,273,647 | 9/1966 | Briggs, Jr. et al. | 166/100 |
| 3,280,917 | 10/1966 | Kisling, III | 166/150 |
| 3,285,344 | 11/1966 | Jensen | 166/149 |
| 3,291,219 | 12/1966 | Nutter | 166/145 |
| 3,305,014 | 2/1967 | Brieger | 166/3 |
| 3,305,023 | 2/1967 | Farley | 166/226 |
| 3,306,102 | 2/1967 | Lebourg | 73/155 |
| 3,308,882 | 3/1967 | Lebourg | 166/3 |
| 3,308,887 | 3/1967 | Nutter | 166/150 |
| 3,319,718 | 5/1967 | Graff | 166/150 |
| 3,356,137 | 12/1967 | Raugust | 166/3 |
| 3,385,364 | 5/1968 | Whitten | 166/100 |
| 3,417,827 | 12/1968 | Smith et al. | 175/4.52 |
| 3,780,575 | 12/1973 | Urbanosky | 73/152 |
| 3,782,191 | 1/1974 | Whitten | 73/155 |
| 3,811,321 | 5/1974 | Urbanosky | 73/155 |
| 3,813,936 | 6/1974 | Urbanosky et al. | 73/155 |
| 3,858,445 | 1/1975 | Urbanosky | 73/155 |
| 3,859,850 | 1/1975 | Whitten et al. | 73/155 |
| 3,864,970 | 2/1975 | Bell | 73/155 |
| 3,924,463 | 12/1975 | Urbanosky | 73/155 |
| 3,934,468 | 1/1976 | Brieger | 73/155 |
| 3,952,588 | 4/1976 | Whitten | 73/155 |
| 4,063,593 | 12/1977 | Jessup | 43/12 |
| 4,248,081 | 2/1981 | Hallmark | 73/151 |
| 4,286,461 | 9/1981 | Bres et al. | 73/155 |
| 4,392,377 | 7/1983 | Rankin | 73/155 |
| 4,535,843 | 8/1985 | Jageler | 166/250 |
| 4,745,802 | 5/1988 | Purfurst | 73/155 |
| 4,754,839 | 7/1988 | Gold | 181/102 |
| 4,938,060 | 7/1990 | Sizer et al. | 73/151 |
| 5,130,950 | 7/1992 | Orban et al. | 367/34 |
| 5,329,811 | 7/1994 | Schultz et al. | 73/155 |
| 5,337,821 | 8/1994 | Peterson | 166/250 |
| 5,377,755 | 1/1995 | Michaels et al. | 166/264 |

APPARATUS AND METHOD FOR ANALYZING A RETRIEVING FORMATION FLUID UTILIZING ACOUSTIC MEASUREMENTS

BACKGROUND OF THE INVENTION

1. Field of the Invention

This invention relates generally to formation fluid testing and collection apparatus and more particularly to a closed-loop system for in situ determining the type and condition of formation fluids in a wellbore and for collecting downhole formation fluid samples under the original formation conditions.

2. Description of the Related Art

In the oil and gas industry, wireline formation testing tools have been used for monitoring formation pressures, obtaining formation fluid samples and for predicting reservoir performance. Such formation testing tools typically contain an elongated body having an elastomeric packer that is sealingly urged against the zone of interest in the wellbore to collect formation fluid samples in storage chambers placed in the tool.

Various types of drilling fluids are used to facilitate the drilling process and to maintain a desired hydrostatic pressure in the wellbore. These drilling fluids penetrate into or invade the formations for varying radial depths (referred to generally as the invaded zones) depending upon the types of the formation and drilling fluid used. Any initial fluid collected by the formation testing tools must first be analyzed to determine when the formation fluid being withdrawn is substantially free of mud filtrates and, thus, to collect only the uncontaminated fluid. Additionally, it is desirable to collect the formation fluids for further analysis in the same condition they exist in the formation. This typically requires that the fluid drawdown pressure be maintained above the bubble point of the fluids. The formation testing tools have utilized various sensors and in situ techniques to determine when the formation fluids being withdrawn are substantially free of mud filtrates and to maintain the drawdown pressure above the bubble point so as to collect clean fluids under the original formation conditions.

Resistivity measurements, downhole pressure and temperature measurements, and optical analysis of the formation fluids have been used to identify the type of formation fluid, i.e., to differentiate between oil, water and gas present in the formation fluid and to determine the bubble point pressure of the fluids. The information obtained from one or more pressure sensors and temperature sensors, resistivity measurements and optical analysis is utilized to control the drawdown rate so as to maintain the drawdown pressure above the bubble point and to determine when to collect the fluid samples downhole. Prior art tools have utilized resistivity measuring devices and temperature sensors as part of a probe assembly to monitor the formation fluid characteristics. Optical fluid analyzers utilizing near-infrared spectroscopy absorption and reflection to differentiate between oil, water and gas have also been used. The fluid from the formation is discharged into the wellbore until the fluid flowing through the flowline is determined to be substantially free from contaminants. The fluid drawrate from the formation is controlled to maintain the drawdown pressure above the bubble point.

The interpretation of the flowline resistivity is difficult and often inaccurate. Interpretation of the resistivity must take fluid dynamics into consideration. The resistivity measured is that of the continuous phase of the fluid in the flowline. A water/hydrocarbon mixture with the water as the continuous phase has a low resistivity that increases due to tortuosity as the percentage of hydrocarbon increases. A water-hydrocarbon mixture with hydrocarbon as the continuous phase can have a high resistivity even if the water volume is large. Flow of alternating slugs of hydrocarbon and water produces noisy resistivity recording. This effect is more evident when gas is present. The optical analyzer provides more accurate results, but is quite expensive and requires the use of sophisticated electronics downhole, which must operate at very high temperatures. Additionally, optical devices tend to become clouded with a thin film which reduces the measurement accuracy.

Thus, a need exists to provide a formation fluid retrieval and collection system that is relatively simple, less expensive than the current state-of-the-art systems and relatively accurate in differentiating between the various types of fluid conditions to ensure that substantially uncontaminated formation fluid samples are collected and that the drawdown pressure is maintained above the bubble point of the formation fluid during the fluid collection process.

The present invention addresses the above-noted deficiencies and provides a relatively simple closed loop system for collecting one or more formation fluid samples under original formation conditions using a novel acoustic cell technique.

SUMMARY OF THE INVENTION

This invention provides a closed-loop system for withdrawing a formation fluid from a zone of interest in a wellbore, in situ determination of the type (single phase or two phase) of the formation fluid being withdrawn, determining the bubble point pressure of the fluid, and for selectively collecting fluid samples above the bubble point pressure of the fluid that are substantially free from any mud filtrates. The closed loop system of the present invention contains an elongated member which has at least one probe that is adapted to be sealingly placed against the wellbore formation. A pump coupled to the probe remotely controls the flow of a fluid from the wellbore formation into a flowline in the elongated member. A pressure sensor provides downhole hydrostatic pressure and an acoustic density cell provides speed of sound in, acoustic impedance of, and acoustic absorption coefficient of the fluid in the flowline. The system determines the density and compressibility of the formation fluid in the flowline from the speed of sound and the acoustic impedance of the fluid and in response thereto controls the fluid flow into the flowline to selectively collect the formation fluid samples that are substantially free from any mud filtrates. The acoustic absorption coefficient is very sensitive to bubbles and aids in maintaining the fluid pressure above the bubble point pressure of the fluid. The absorption coefficient is also sensitive to the fluid viscosity which aids in distinguishing among hydrocarbons.

This invention provides a method for retrieving and collecting formation fluids from a zone of interest in a wellbore at the original formation conditions. The method of the invention contains the steps of: (a) sealingly placing a probe against the zone of interest in the wellbore for receiving the formation fluid; (b) controllably allowing the fluid to pass from the probe into a flowline; (c) determining the speed of sound in the fluid, the acoustic impedance and acoustic absorption coefficient of the fluid in the flowline; (d) determining the density and compressibility of the fluid from the speed of sound in the fluid, acoustic impedance and acoustic absorption coefficient of the fluid in the flowline; (e)

controlling the flow of the fluid into the flowline based on the fluid density and compressibility so as to maintain the fluid pressure in the flowline above the bubble point pressure of the fluid; and (f) collecting a sample of the fluid from the flowline into a downhole storage chamber maintained at a pressure above the bubble point pressure of the fluid.

Examples of the more important features of the invention thus have been summarized rather broadly in order that detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

For detailed understanding of the present invention, references should be made to the following detailed description of the preferred embodiment, taken in conjunction with the accompanying drawings, in which like elements have been given like numerals and wherein.

DESCRIPTION OF THE PREFERRED EMBODIMENT

Figure 1A:
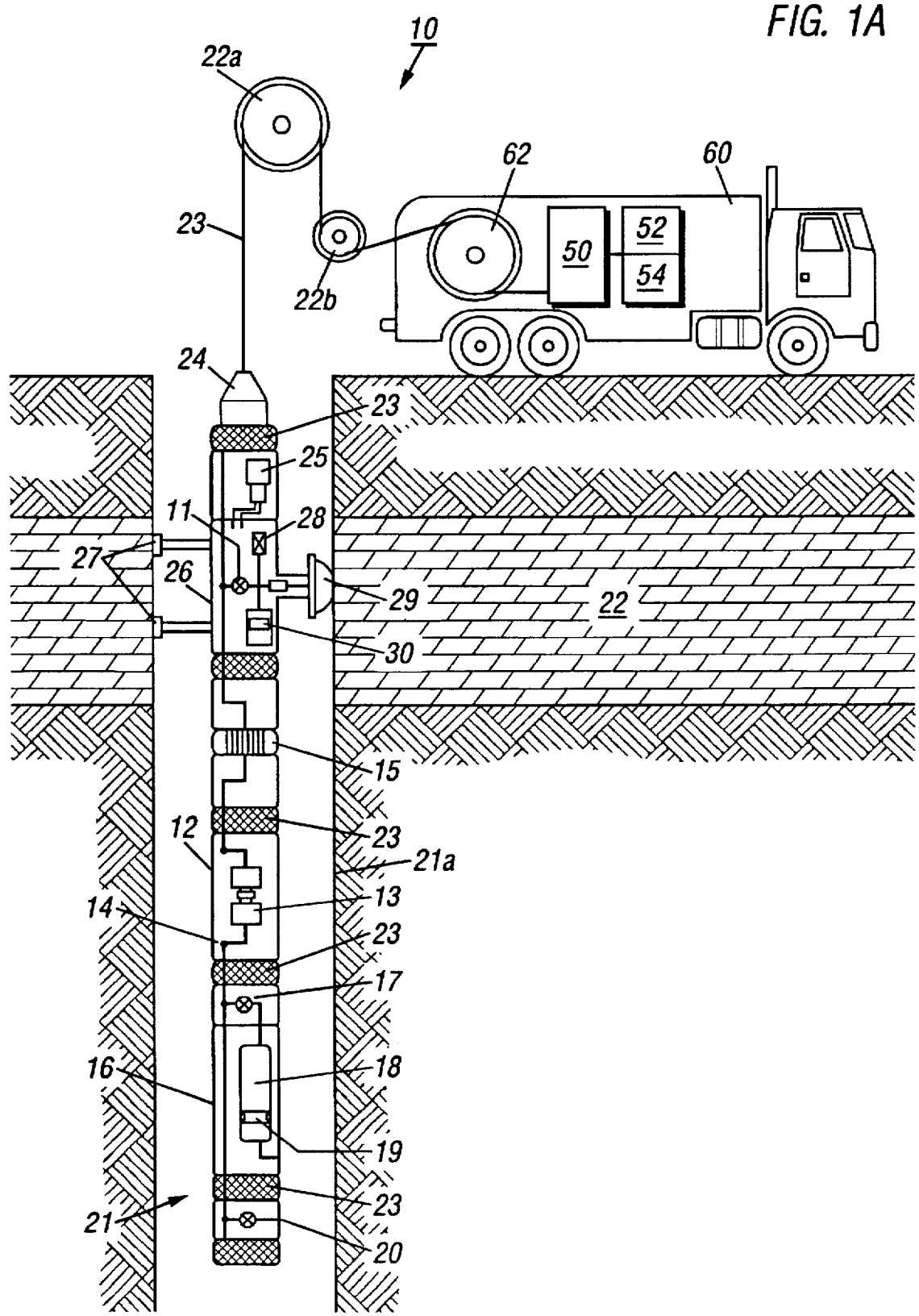
FIG. 1A shows a schematic elevational view of a system having a sectional formation evaluation tool conveyed in a wellbore for testing and retrieving formation fluids according to the present invention.

FIG. 1A shows an embodiment of a wireline formation evaluation and testing system 10 having a downhole formation evaluation and testing tool (apparatus) 24 conveyed in a wellbore 21 by a wireline 23' for testing and retrieving formation fluids from desired formations within the wellbore 21 according to the normal operation of the system 10. The tool 24 contains a number of functional modules which are serially coupled to form the tool 24 that suits the needs in a particular test situation. In the embodiment of FIG. 1A, the tool 24 includes a sequential arrangement of an electro-hydraulic system 25, a packer/probe module 26, an acoustic density cell module 15, a flushing pump module 12, a sampling module 16, and a test equalization valve 20. The tool 24 is conveyed in the wellbore by the wireline (cable) 23' which contains a plurality of conductors for providing power to the various components in the tool 24 and for providing two-way electrical and data communication between the tool 24 and a control unit 50, which is usually placed uphole in a suitable truck 60 for land operations and in a cabin (not shown) for offshore operations. The wireline 23' is conveyed by a drawworks 62 via a system of pulleys 22a and 22b.

The control unit 50 contains a computer and associated memory for storing therein desired programs and models. The control system 50 controls the operation of the tool 24 and processes online data received from the tool 24 during operation of the tool 24. The control unit 50 is coupled to a variety of peripherals, such as a recorder 52 for recording data and a display/monitor 54 for displaying desired information during operation. The use of the control unit 50, display/monitor 54 and recorder 52 is known in the art of well logging and is, thus, not explained in greater detail herein.

Figure 1B:
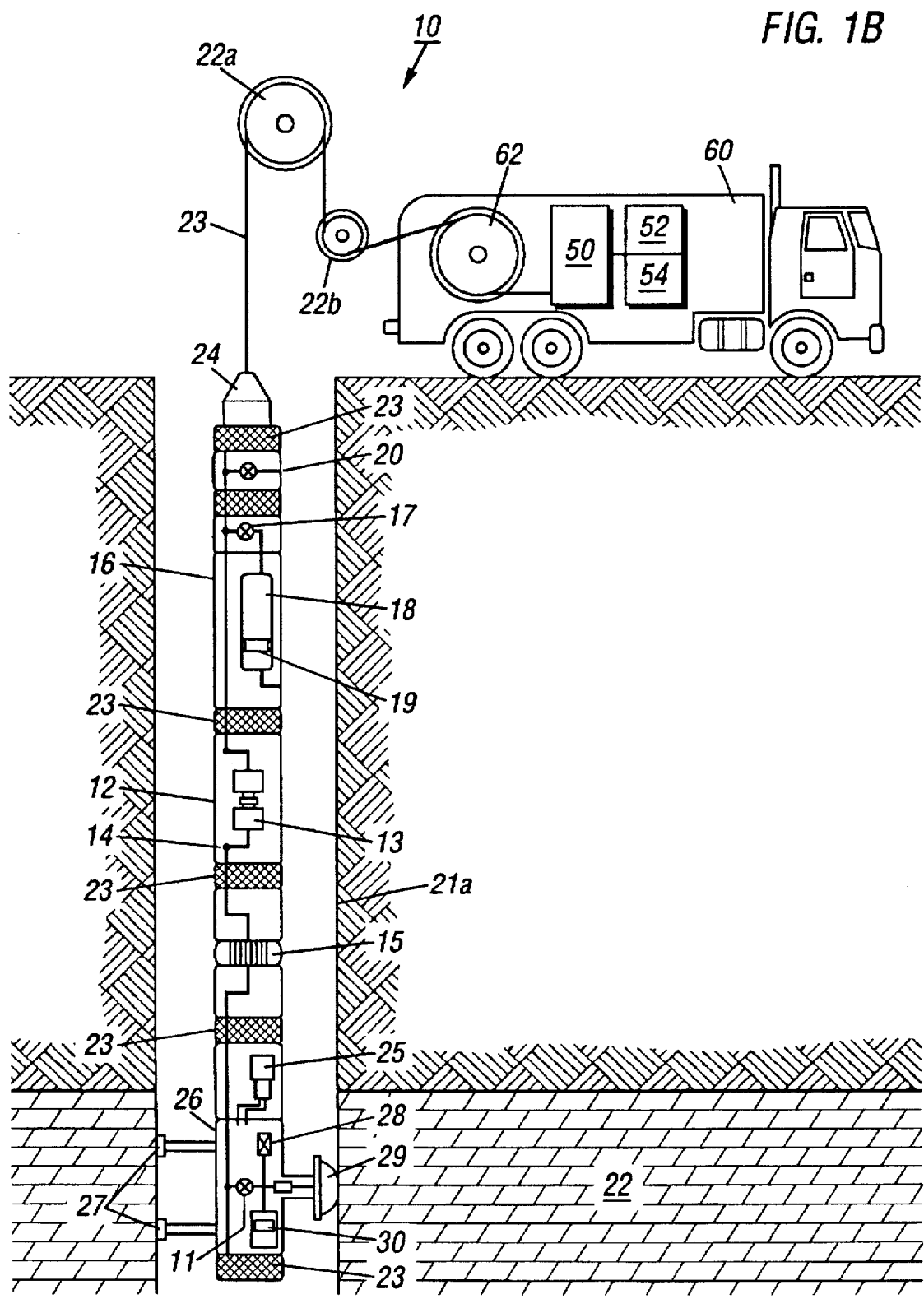
FIG. 1B shows a schematic elevational view of the system of FIG. 1A utilizing an alternative sectional arrangement for the formation evaluation tool.

FIG. 1B shows a schematic view of an alternative arrangements of the various sections of the tool 24. In this embodiment, the packer/probe section 26 is placed near the bottom of the tool string for rathole type testing. The sequential arrangement of the sections contains the test equalization valve 20, sampling section 16, flushing pump section 12, sonic density cell section 15, electro-hydraulic system 25, and formation tester packer/probe section 26.

Figure 1C:
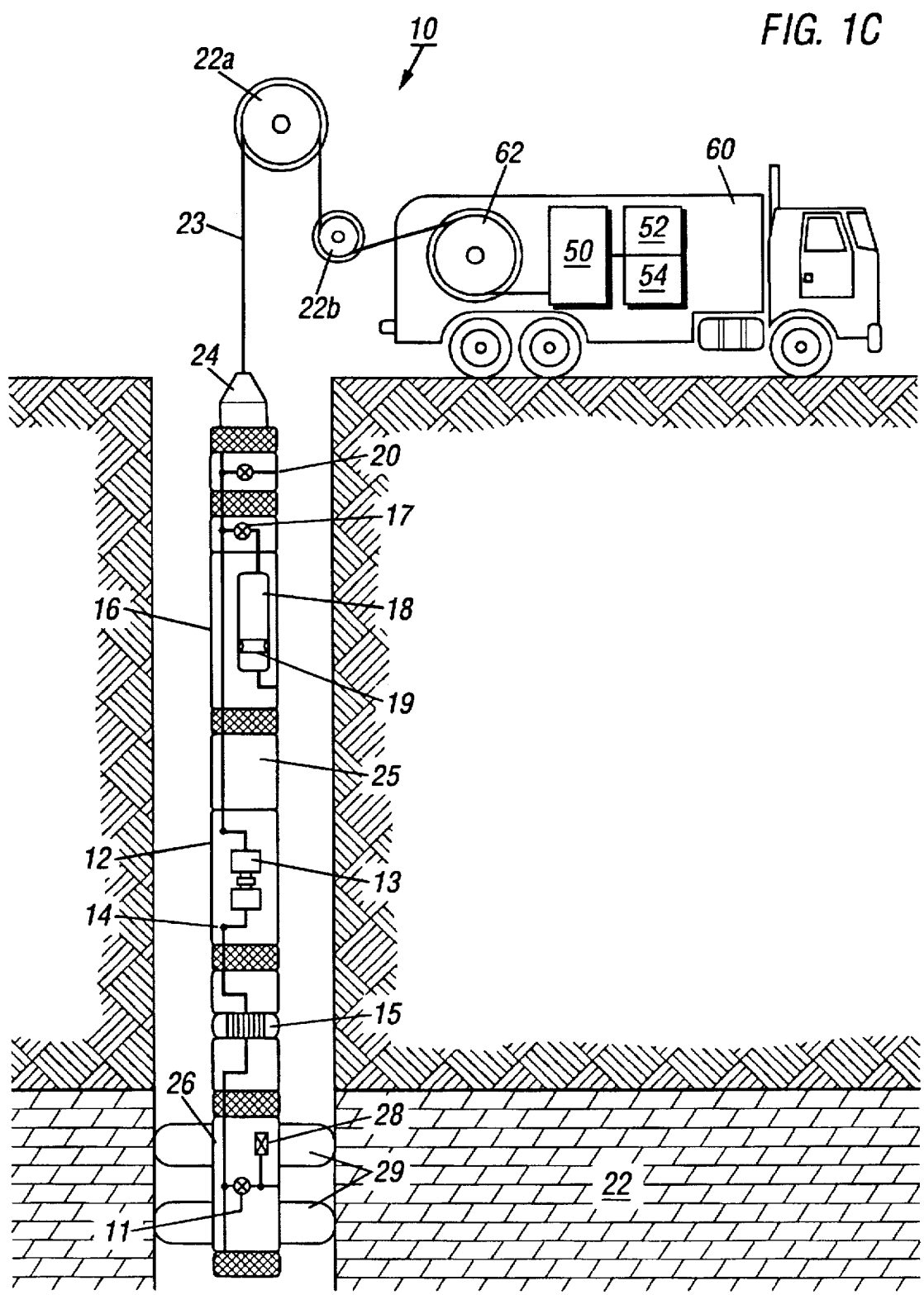
FIG. 1C shows a schematic elevational view of the system of FIG. 1A utilizing an alternative sectional arrangement for the formation evaluation tool.

FIG. 1C shows a schematic view of the system of FIG. 1A having yet another arrangement of the various tool sections. The sequential order of the sections in the embodiment of FIG. 1C is the same as that of the embodiment shown in FIG. 1A except that the packer/probe section 26 contains multiple packer/probe units and utilizes inflatable packers as the backup pads.

Referring back to FIG. 1A, the formation tester packer/probe section 26, contains one or more inflatable packers/probes 29, each such packer/probe being adapted to be sealingly urged against the wellbore wall 21a. One or more backup pads 27 are urged against the wellbore wall 21a opposite the packer/probe 29. The electro-hydraulic section 25 is utilized to inflate the pads of the packer/probe 29 to seal it against the interior of the wellbore 21. The electro-hydraulic section 25 also deploys backup pads 27 to cause the packer/probe 29 to urge against the wellbore wall 21a. Any other suitable means may also be used for deploying packer/probe section 26 for the purposes of this invention. Each packer/probe section 26 contains a probe (not shown) radially extending away from the tool body and is adapted to penetrate into the formation 22 when the packer/probe 29 is urged against the wellbore interior 21a. The packer/probe section 26 also contains a pressure gauge 28 to monitor pressure changes during fluid sample collection process, an isolation valve 11 for use during flushing operations, and a pretest piston 30 for drawing samples during pretesting.

Still referring to FIG. 1A, the acoustic density cell 15 is adapted to receive fluid flow through the probe of packer/probe 29, which is more fully explained later in reference to FIG. 2. A flushing pump section 12 containing a flushing pump 13 is adapted to receive the fluid passing through the acoustic cell 15 via a flowline 14 where the fluid is directed in to the sampling section 16. The sampling section 16 contains a sample chamber valve 17, which is opened to direct the formation fluid to one or more sample chambers 18 for collecting formation fluid therein. When the sample chamber valve 17 is closed, the fluid is discharged into formation borehole 21. The sample chamber valve 17 may be controlled downhole or from the surface by the control unit 50. An equalization valve 20 is provided to maintain a desired pressure in the flowline 14. The equalization valve is closed during sample collection and closed during the flushing operation. A piston 19 is used to control the fluid pressure during sample collection to assure that the sample fluid does not separate out in to two phases,i.e., gas and liquid. Different sections of the tool 24 are suitably connected to each other by means of section connectors, generally designated by numeral 23.

Figure 2:
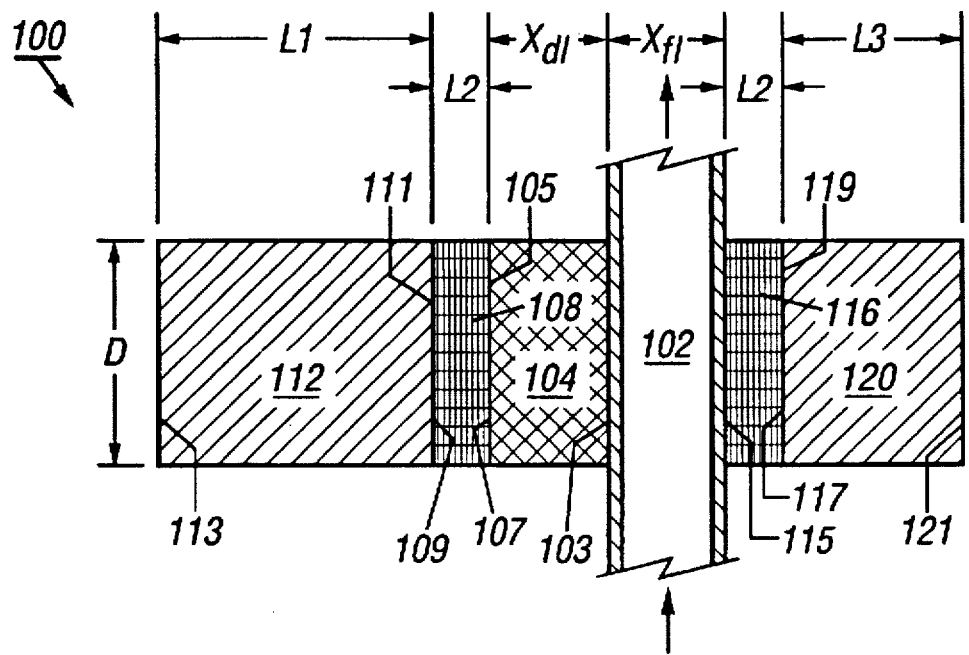
FIG. 2 shows an elevational cross-section of an embodiment of the sonic density cell for use in the formation evaluation tool according to the present invention.

FIG. 2 shows an elevational cross-section of one embodiment of an acoustic density cell 100 according to the present invention. The acoustic density cell 100 contains a delay line 104 of thickness $X_{d1}$ having opposing surfaces 103 and 105. The surface 103 is in close acoustic contact with a fluid flowline 102 through which the formation fluid flows during the testing and collection of the formation fluid. The delay line 104 material may be a machineable glass or any other suitable material that would sufficiently delay the acoustic signal passing therethrough, preferably by a time that exceeds the transducer ringdown time, and have an acoustic impedance between the impedance of the piezoelectric material used in the transducer and the formation fluid. Such a delay line enables measuring the acoustic impedance of the fluid. An acoustic transducer 108 (transducer 1) of thickness L2 having a opposing surfaces 107 and 109 is placed against the delay line 104. The transducer 108 may be used as an acoustic signal transmitter or a receiver. The transducer 108 preferably is made of a suitable piezoelectric material but is not limited to such a material. The surface 105 of the delay line 104 and the surface 107 of the transducer 108 are preferably bonded together. A backing 112 of thickness $L_1$ is placed against transducer 108 so that the surface 111 of the backing is in contact with the transducer 108. The backing 112 is preferably made of a mixture of tungsten and a rubber material but is not limited to such a composition. The backing material 112 preferably has a high acoustic absorption coefficient and an acoustic impedance that will minimize the acoustic reflection from the surface 111. The thickness $L_1$ is made sufficiently large so as to minimize reflections from the surface 113. The surface 109 of the transducer 108 and the surface 111 of the backing 112 are preferably bonded together.

A second acoustic transducer 116 (transducer 2) of thickness $L_2$ having opposing surfaces 115 and 117 is placed against the flowline 102 across from the delay line 104. The transducer 116 also is preferably made of piezoelectric material but may be made of any other suitable material. The surface 115 of the transducer 116 is in close acoustic contact with the fluid flowline 102. A backing 120 of thickness $L_3$ having opposing surfaces 119 and 121 is placed against the transducer. The surface 117 of the transducer 116 and the surface 119 of the backing 120 are preferably bonded together. In the preferred embodiment, the delay line 104, first transducer 108, backing 112, second transducer 116, and backing 120 preferably have the same depth D.

Figure 3:
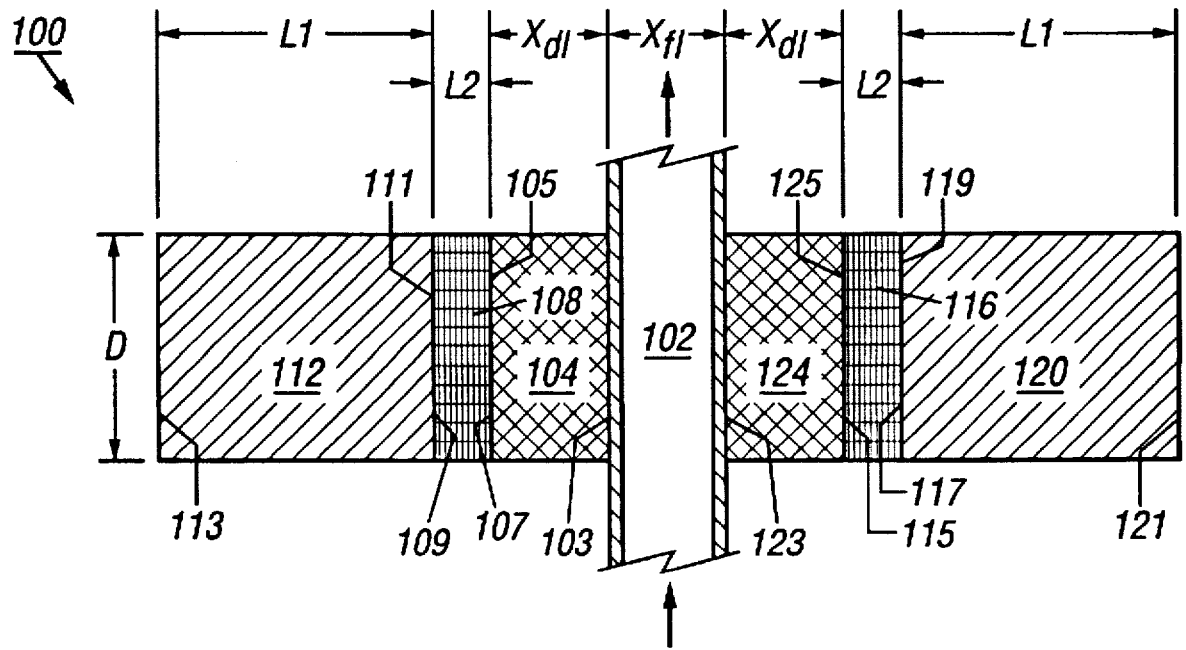
FIG. 3 shows an elevational cross-section of an alternative embodiment of the sonic density cell for use in the formation evaluation tool.

FIG. 3 shows an elevational cross-section of an alternative embodiment of the sonic density cell 100 according to the present invention. In this embodiment, the elements shown on the left of the fluid flowline 102 in FIG. 3 are identical to the elements shown in FIG. 2. The elements to the right of the fluid flowline 102 in FIG. 3 are a minor image of the elements to the left of the fluid flowline 102. In the embodiment shown in FIG. 3, a delay line 124 of thickness $X_{d1}$ has a surface 123 in close acoustic contact with the fluid flowline 102 opposite the delay line 102. A backing 120 of thickness L1 having surfaces 119 and 121 is placed against the transducer 116. The surface 115 of the transducer 116 is preferably bonded to the surface 125 of the delay line 124. The surface 117 of the transducer 116 and the surface 119 of the backing 120 are preferably bonded together. The advantages of this embodiment are that the transducers 108 and 116 are isolated from the fluid, the two sides of the sonic density cell are identical in design and the acoustic impedance of the fluid may be averaged for surfaces 103 and 123. The overall size of the sonic density cell 100, however, is somewhat increased.

The dimensions of the elements in the preferred embodiment of the sonic density cell 100 are (in inches): $L_1$=2.0, $L_2$=0.1, $X_{df}$=0.6, $X_{fl}$=0.25, and D=1.0. The signal frequency applied to the transmitters may be varied from 0.3 to 10 mega hertz (MHz) depending on the materials used and the dimensions of the elements in constructing the sonic density cell 100. For a single phase flow in the flowline 102 the frequency of the signals transmitted through the fluid from one transducer to the other may be varied to obtain the viscosity of the fluid. For two phase flow, viscosity and also scattering from the second phase in the continuous phase affect the frequency of signals passing through the fluid. The dimensions and signal frequencies indicated herein can be easily varied to suit different test scenarios and they are not intended as any limitations on the embodiment of the sonic density cell 100.

Figure 4A:
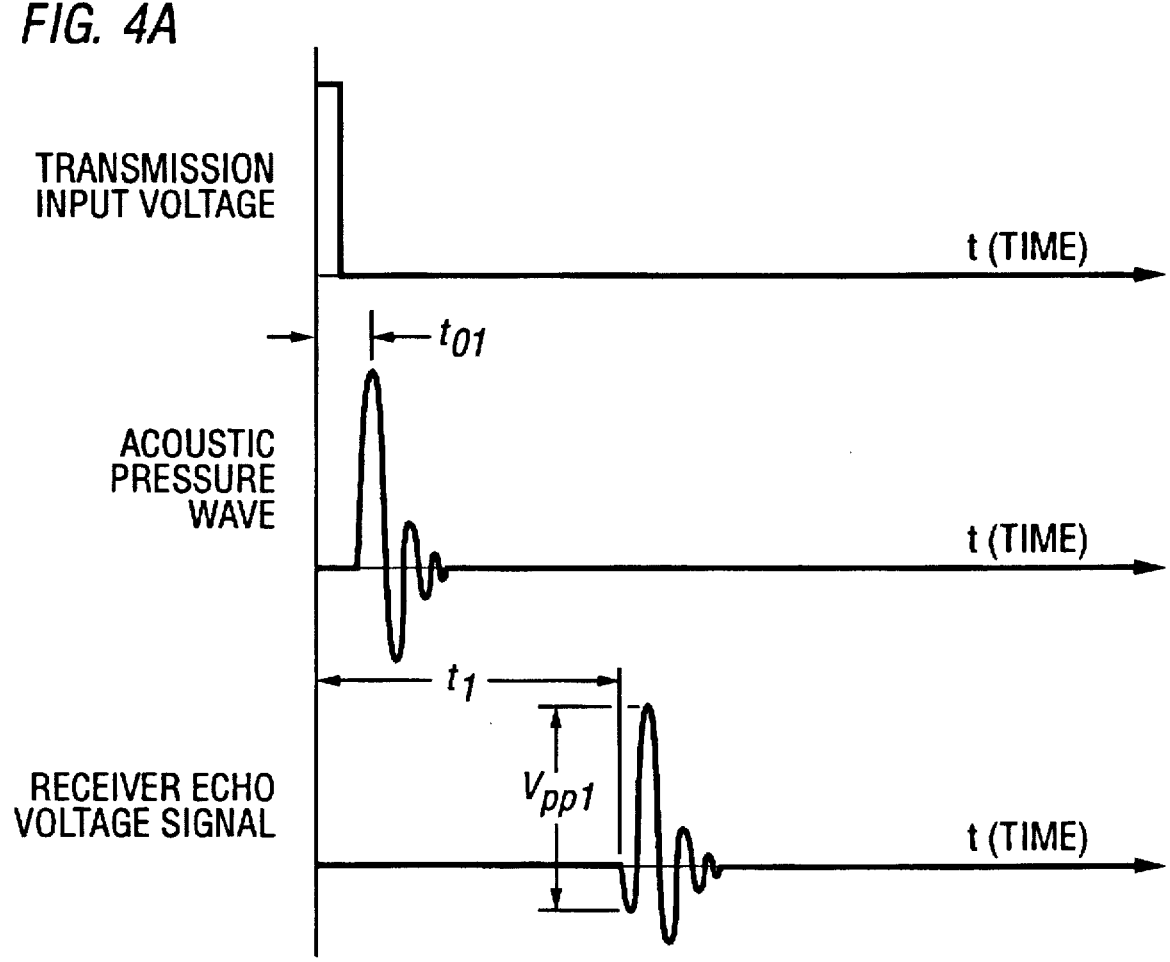
FIG. 4A shows typical waveforms of input electrical signal to and generated acoustic pressure wave by the transmitter 108 of the density cells, and waveform of the acoustic echo signal received by the receiver of the density cells shown in FIG. 2.
Figure 4B:
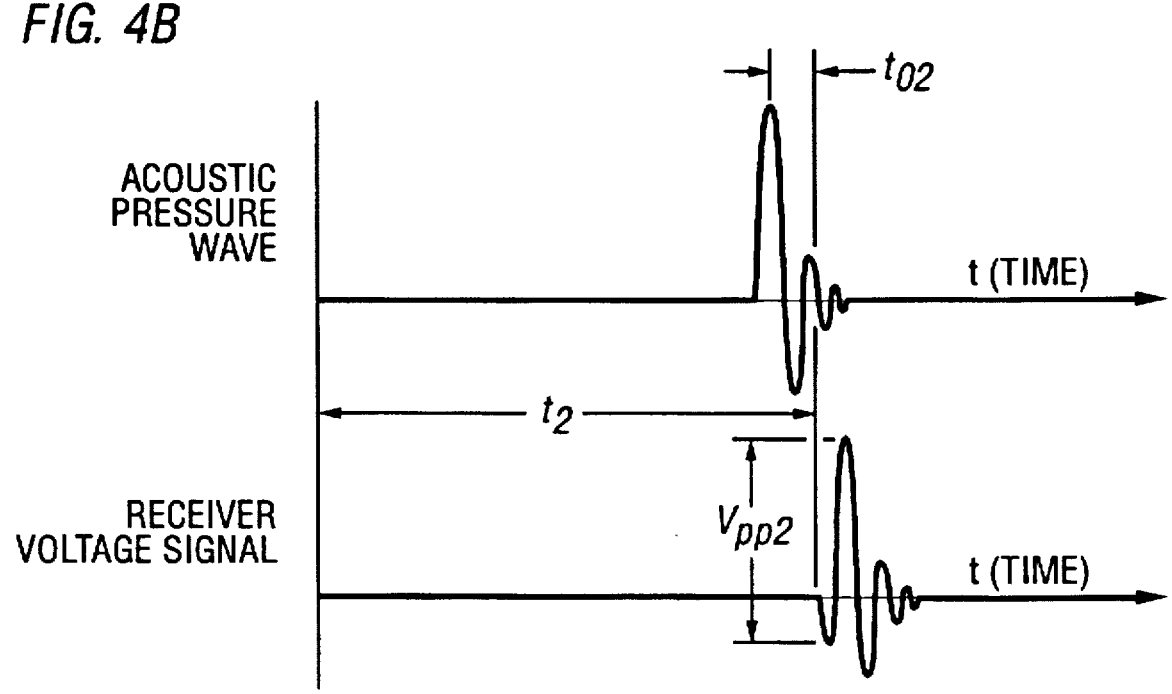
FIG. 4B shows waveforms of received acoustic pressure wave and the resulting electrical voltage signal produced by transducer 116 of FIG. 2.

FIG. 4A shows typical waveforms of input electrical signal, generated acoustic pressure wave, and received acoustic echo signal for the transmitter/receiver transducer 108 of FIG. 2. Now referring to FIGS. 2, 4A, and 4B, when an electrical signal of amplitude $V_0$ is applied to the transducer 108, an acoustic pressure wave shown in FIG. 4A is produced after a short time delay ($t_{01}$). This acoustic pressure wave travels in all adjacent media. Whenever an acoustic wave encounters a new medium, a fraction of the wave amplitude is reflected and a fraction of the wave amplitude is transmitted through the new medium. The reflected wave from the interface of the delay line 104 and the test fluid flowing through the fluid flowline 102 provides a measure of the acoustic impedance of he fluid. The resultant echo signal of amplitude $V_{pp1}$ is received by the transducer 108 at time $t_1$. The time difference ($t_1-t_{01}$) is related to the speed of sound in the delay line 104. The signal amplitude $V_{pp1}$ of the echo is also related to the acoustic impedances of the material of the delay line 104 ($Z_{dl}$) and that of the fluid interface ($Z_{fl}$). After the acoustic wave transmitted into the fluid travels through the fluid, the second transducer 116 detects its arrival at time $t_2$ with an amplitude $V_{pp2}$.

A short time delay $t_{02}$ occurs between the arrival of the acoustic wave at the transducer 116 and the electronic detection of the signal. The time $t_2$ is related to the speed of sound through the delay line 104 and the speed of sound through the fluid path in the fluid flowline 102. The amplitude $V_{pp2}$ of the signal received by the transducer 116 is related to the acoustic signal transmission and attenuation through the delay line 104 and through the fluid in the fluid flowline 102.

Physical properties of the delay line 104 material may be determined in the laboratory by known calibration procedures. Utilizing the acoustic density cell 100 measurements and the parameters of the properties of the delay line 104, the density and compressibility of the test fluid may be determined using equations 1 through 14 given below. Also, acoustic attenuation coefficient (a) of the test fluid may be determined using the acoustic density cell 100 measurements and equations 15 through 18 given below.

Fluid Density and Compressibility Calculations
Acoustic impedance for fluid and delay line:

$$Z_{fl} = c_{fl}\rho_{fl} \quad \quad 1)$$

$$Z_{dl} = c_{dl}\rho_{dl} \quad \quad 2)$$

Acoustic sound speed and wave length for fluid and delay line material:

$$c_{fl} = \frac{x_{fl}}{t_{fl}} \quad \quad 3.)$$

$$c_{dl} = \frac{x_{dl}}{t_{dl}} \quad \quad 4.)$$

$$\lambda_{fl} = \frac{c_{fl}}{f_{fl}} \quad \quad 5.)$$

$$\lambda_{dl} = \frac{c_{dl}}{f_{dl}} \quad \quad 6.)$$

Relationship of the echo time measured by transducer 1 to the delay time:

$$t_1 = 2\cdot(t_{o1}+t_{dl}) \quad \quad 7)$$

Solving for delay line time:

$$t_{dl} = \frac{t_1}{2} - t_{o1} \quad \quad 8.)$$

Relationship of the received signal in transducer 2 to the fluid time and delay time:

$$t_2 = t_{o1} + t_{dl} + t_{o2} + t_{fl} = \frac{t_1}{2} + t_{o2} + t_{fl} \quad \quad 9.)$$

Solving for the fluid time:

$$t_{fl} = t_2 - \frac{t_1}{2} - t_{o2} \quad \quad 10.)$$

The reflectance measured by transducer 1:

$$R_1 = \frac{V_{pp1}}{K_1 V_o} = \left(\frac{Z_{fl}-Z_{dl}}{Z_{fl}+Z_{dl}}\right) \quad \quad 11.)$$

Solving for the fluid acoustic impedance:

$$Z_{fl} = Z_{dl}\left(\frac{1+\frac{V_{pp1}}{K_1 V_o}}{1-\frac{V_{pp1}}{K_1 V_o}}\right) \quad \quad 12.)$$

Solving for the fluid density:

$$\rho_{fl} = \frac{Z_{fl}}{c_{fl}} = \frac{Z_{dl}}{c_{fl}}\left(\frac{1+\frac{V_{pp1}}{K_1 V_o}}{1-\frac{V_{pp1}}{K_1 V_o}}\right) = \quad \quad (13.)$$

$$\rho_{dl}\frac{x_{dl}}{x_{fl}}\left(\frac{t_2-\frac{t_1}{2}-t_{o2}}{\frac{t_1}{2}-t_{o1}}\right)\left(\frac{1+\frac{V_{pp1}}{K_1 V_o}}{1-\frac{V_{pp1}}{K_1 V_o}}\right)$$

The fluid compressibility can now be determined from the density and sound speed:

$$\gamma_{fl} = \frac{1}{\rho_{fl}c_{fl}^2} = \frac{1}{\rho_{fl}}\left(\frac{t_2-\frac{t_1}{2}-t_{o2}}{x_{fl}}\right)^2 \quad \quad 14.)$$

Fluid Attenuation and Calculations
Delay line to fluid acoustic transmission:

$$T_{dl-fl} = \frac{2\cdot Z_{fl}}{Z_{dl}+Z_{fl}} \quad \quad 15.)$$

Fluid to transducer 2 acoustic transmission:

$$T_{fl-2} = \frac{2\cdot Z_2}{Z_{fl}+Z_2} \quad \quad 16.)$$

Relationship of the measured peak to peak voltage received in transducer 2:

$$V_{pp2} = K_1 V_o T_{dl-fl} e^{(-\alpha x_{fl})} \cdot K_2 T_{fl-2} \quad \quad 17)$$

Solving for the attenuation coefficient:

$$\alpha = -\left(\frac{1}{x_{fl}}\right)\ln\left(K_1\cdot T_{dl-fl}\cdot K_2\cdot T_{fl-2}\cdot\left(\frac{V_o}{V_{pp2}}\right)\right) \quad \quad 13.)$$

Nomenclature used herein is as follows:
Variables:
V—voltage
c—speed of sound
γ—compressibility
λ—wave length
ρ—density
f—frequency
x—distance
Z—acoustic impedance
R—acoustic reflectance
T—acoustic transmission
Subscripts:
1-transducer 1, transmitter/receiver
2-transducer 2, receiver
pp-peak to peak voltage
fl-fluid
dl-delay line
Calibration and known values:
$c_{dl}$—sound speed of delay line material
$\rho_{dl}$—density of delay line material
$t_{o1}$—offset time for transducer 1 electronic delay
$t_{o2}$—offset time for transducer 2 electronic delay
$x_{dl}$—thickness of delay line
$x_{fl}$—thickness of fluid passage
$V_o$—calibration voltage
$K_1$—calibration constant for transducer 1
$K_2$—calibration constant for transducer 2
Measured values:
$t_1$—time for echo signal for transducer 1
$t_2$—time for received signal for transducer 2
$V_{pp1}$—peak to peak voltage for echo signal for transducer 1
$V_{pp2}$-peak to peak voltage for received signal for transducer 2

The nomenclature used in the above equations is as follows: The acoustic attenuation coefficient (a) of a two phase fluid, e.g. liquid and gas, depends on the percentages of the two constituents. Acoustic attenuation coefficient of fluids containing known percentages of the two constituents can be determined in the laboratory. A graph plot of the laboratory measured acoustic attenuation coefficient as a function of the percentage of gas component in the fluid can be obtained. This acoustic attenuation depends on the viscosity, frequency and the size of the second phase in the continuous phase.

Figure 5:
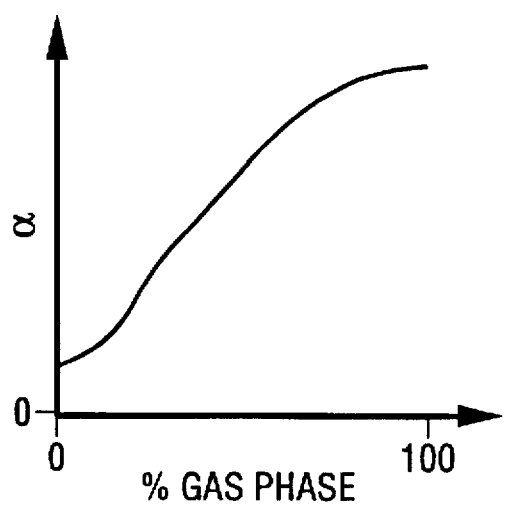
FIG. 5 shows a typical plot of the acoustic absorption coefficient (a) as a function of the percentage of gas phase content in a fluid.

FIG. 5 shows a typical plot of the acoustic attenuation coefficient (a) as a function of the percentage of gas phase content in a fluid when the other parameters remain constant. The fraction of the gas in the fluid b can be determined numerically by making a polynomial curve fit of the laboratory measured data to the plot in FIG. 5. This polynomial fit is then compensated for the effects of viscosity and the second phase distribution. This compensation is preferably achieved by regression methods on known two-phase fluids. A typical formation is developed according to equation (19) given below. Thus, using measurements from the sonic density cell 100, the acoustic absorption coefficient of the test fluid is calculated according to equation (18) described earlier, and then the fraction of the gas phase is determined according to equation (19).

$$b = A_0 + B_0 a + C_0 a^2 + D_0 a^3 + E_0 f + F_0 f^2 + G_0 f^3 + H_0 R \quad (19)$$

The above equation requires broadband acoustic transmitters and spectral analysis of the received signals to perform frequency (f) and pressure (p) compensation. The spectral dependance of a provides the spectral dependence of b. The empirical measurements on known two-phase fluids can be made in the laboratory to interpret the fraction of the gas phase from the frequency dependence of equation (19). The frequency dependancies of viscosity and two phase scattering differ. Equation 19 sibtracts viscosity effects to improve the accuracy of calculating b.

To operate the system of the present invention, the tool 24 is lowered into the wellbore 21 by means of the wireline 23' to a desired depth. The packer/probe 29 is urged against the wall of the wellbore 21 at the zone of interest in the formation 22. The electro hydraulic system 25 deploys the probe of the packer/probe 29 and backup pads 27 to create a hydraulic seal with the elastomeric packer/probe 29 against the formation 22. Normally the tool equalization valve 20, the sample chamber valve 17 and the isolation valve 11 remain closed during the packer/probe 29 deployment. The pretest piston 30 is used to draw a small sample of fluid into the flowline 14 of the tool 24 while the flowline 14 is monitored using a high accuracy quartz pressure gauge 8. As the fluid sample is drawn into the flowline 14 of the tool 24 the pressure decreases due to the resistance of the formation 22 to fluid flow. When the pretest stops, the pressure in the flowline 14 increases until it equalizes with the pressure in the formation 22. This is due to the formation 22 gradually releasing the fluids into the probe of the packer/probe 29. The formation pressure is typically lower than the borehole 21 or hydrostatic pressure and this difference is used as a means for verifying that the packer/probe 29 is sealed against the wall of the borehole 21. The fluids in the pore space of the formation 22 near the probe of the packer/probe 29 are typically invaded with the mud filtrate fluids.

To obtain a sample that is representative of the in situ formation fluids the area near the probe needs to be flushed or pumped until formation fluids are flowing into the tool 24. To flush the area near the probe of the packer/probe 29, the isolation valve 11 and the equalization valve 20 are opened, and the flushing pump 13 is started. The flushing pump 13 is preferably a double acting piston pump so that the fluid flow will be constant and as uniform as possible. However, this invention is not limited to a particular type of flushing pump and any suitable means may be used to serve the stated purpose. The flushing pump 13 draws fluid into the probe of the packer/probe 29 and expels fluid at hydrostatic pressure out of the equalization valve 20.

The pumping rate of the flushing pump 13 is regulated such that the pressure in the flowline 14 near the probe is maintained above the bubble point of the fluid sample. While the flushing pump is running, the sonic density cell 15 is used to measure the fluid properties. The sonic density cell 15 can monitor the density of the fluid, sound speed in the fluid, bulk modulus of the fluid, and presence of gas bubbles in the fluid. By monitoring the formation of gas bubbles in the fluid, the flow in the flowline 14 can be constantly adjusted so that a single phase fluid is maintained by regulating speed of the flushing pump 13.

The aforementioned fluid properties are of the type of fluid in the flowline 14 and knowledge of the fluid properties can be used to monitor the fluid flow while the formation fluid is being pumped for sample collection. Thus when it is determined that the formation fluid flowing through the flowline 14 is representative of the in sire conditions, the sample chamber valve 17 is opened and the equalization valve 20 is closed. The flushing pump 13 continues to pump the formation fluid through the flowline 14 and the fluid is directed into the sample chamber 18 until it is filled. The flushing pump 13 may continue to pressure the collected sample in the sample chamber 18 to a desired pressure level to assure in situ pressure level, and then all of the valves, the isolation valve 11, the sample chamber valve 17, and the equalization valve 20 are closed.

The bubble point of the fluid in the flowline 14 is measured by using the sonic density cell 15 in conjunction with the flushing pump 13. The flushing pump 13 is used to lower the pressure in the flowline 14 between the isolation valve 11 and the flushing pump 13. The sonic density cell 15 determines the density change of the fluid and bubble formation in the flowline 14. A pressure gauge (not shown) is also used to determine the bubble point of the fluid.

The configuration of various sections in the tool 24 may be changed to suit the test conditions but it is desirable for the sonic density cell 15 to be placed between the flushing pump 13 and the packer/probe section 29 to enable monitoring of the fluid properties on the low pressure side of the flushing pump 13. As discussed earlier, FIG. 1B shows an alternative embodiment of the tool 24 wherein the packer/probe section 29 is near the bottom of the string of the probe section 29 in tool 24 for rathole type testing. FIG. 1C shows yet another embodiment of the tool 24 with an inflatable packer section of the packer/probe 29 rather than a single packer/probe unit. Additionally, multiple packer/probe sections can be used instead of a single packer/probe section 29 but the basic operation of the tool 24 remains the same.

Figure 6:
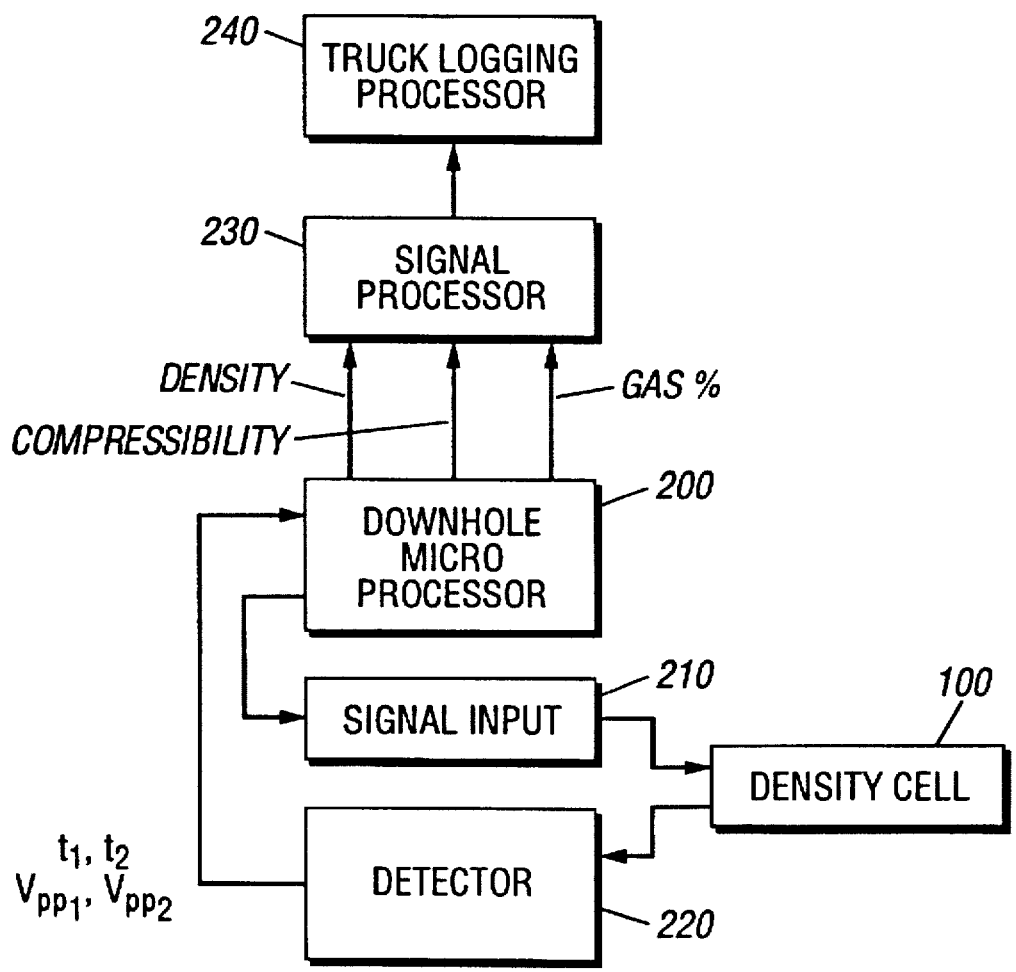
FIG. 6 shows a block diagram of the circuit for transmitting, receiving and recording signals to and from the sonic density cell and other modules of the tool.

FIG. 6 shows a functional block diagram for recording signals from the sonic density cell 15 and other tool sections. Referring now to FIGS. 1A, 2, 4A, 4B and 6, the truck logging processor 240 contains a control unit 50 for controlling the operation of the tool 24, a display monitor 52 for displaying the operator commands and the real time results from the tool 24, and a recorder 54 that records desired signals to and from the tool 24. A downhole microprocessor 200 (preprogrammed or operator controlled) instructs the signal input generator 210 to apply electrical signal shown in FIG. 4A to transducer 1 108. The echo signal received by transducer 108 after time $t_1$ and electrical signal generated by the transducer 116 after time $t_2$ are communicated to the downhole microprocessor 200. The downhole microprocessor 200 computes the fluid density, the fluid compressibility, percentage of gas content in the test fluid and communicates the signals to signal processor 230. Information received by the signal processor is communicated to the track logging processor 240 where it processed, recorded and monitored by the testing personnel.

As noted earlier, the initial fluid drawn from the formation 22 typically contains mud filtrates which have invaded into the formation 22. It is, therefore, important that the formation fluids collected downhole be uncontaminated (clean fluid) and in the same physical conditions in which such fluids are present in the formation. For example, the gas and oil contents of the fluid should be maintained in the manner present in the formation during the collection process. This requires determining when the fluid flowing through the flowline is substantially free of mud filtrates and collecting the fluid above the bubble point pressure of the fluid. As noted earlier, the prior art tools utilize resistivity measurements and optical means to continuously determine the downhole conditions of the fluid during the collection process and to control the flow rate to maintain the fluid pressure above the bubble point. Such apparatus and method are complex and are usually are very expensive, susceptible to contamination and very reliable. When a desired amount of the fluid has been collected in the fluid chamber 18, a new command signal may be sent downhole to select other chambers or to stop the operation of the pump 17 or to reverse the cycle and start another cycle, if necessary.

To determine the bubble point pressure, the formation fluid flow rate into the flowline 14 is slowly increased by controlling the flush-pump 13 while continuously monitoring the fluid density and the fluid compressibility. As the fluid rate is increased, the gas in fluid, if present, will expand into a gaseous state from its normal liquid state which it is present in the formation, which will be observed as a sudden decrease in the density. The pressure at which the density drops is the bubble point pressure of the fluid. To ensure the accuracy of the results, the flow rate is decreased until the density suddenly rises to the initial value of the clean fluid and the corresponding fluid pressure. The procedure may be repeated if necessary to accurately determine the bubble point pressure.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. An apparatus for testing and retrieving formation fluid from a wellbore formation, comprising:
   (a) a probe adapted for placement against the formation for withdrawing the formation fluid into a flowline used for retrieving said formation fluid;
   (b) a pump for controlling the flow rate of the formation fluid into the flowline; and
   (c) an acoustic device for providing signals for determining characteristics of the formation fluid in the flowline, said acoustic device having a transducer for transmitting acoustic signals through the fluid in the flowline and a receiver for detecting acoustic signals passing through the fluid in the flowline.

2. The apparatus as specified in claim 1, wherein the acoustic device further has a first delay line placed between the acoustic transmitter and the flowline so as to cause the acoustic signals to pass through the delay line before reaching the flowline.

3. The apparatus as specified in claim 2, wherein the acoustic device further has a second delay line placed between the acoustic receiver and the flowline so as to cause the acoustic signals from the acoustic transmitter to pass through the second delay line before reaching the receiver.

4. The apparatus as specified in claim 3, wherein the delay in the first and second delay lines are substantially identical in composition and size.

5. The apparatus as specified in claim 1 further having a control circuit for determining the characteristics of the fluid in the flowline.

6. The apparatus as specified in claim 5, wherein the control circuit controls the flow of the fluid into the flowline as a function of the determined characteristics of the fluid.

7. The apparatus as specified in claim 6, wherein the fluid characteristics include density of the fluid in the flowline.

8. The apparatus as specified in claim 7, wherein the fluid characteristics include compressibility of the fluid in the flowline.

9. The apparatus as specified in claim 6, wherein the control circuit controls the flow of the formation fluid so as to maintain the pressure in the flowline above the bubble point pressure of any gas in the formation fluid in the flowline.

10. The apparatus as specified in claim 9 further having a chamber for receiving formation fluid from the flowline.

11. The apparatus as specified in claim 9, wherein the control circuit is operatively coupled to the pump and controls the pump to control the formation fluid flow rate into the flowline as a function of the fluid density and compressibility so as to maintain the flowline pressure above the bubble point pressure of any gas contained in the formation fluid in the flowline.

12. The apparatus as specified in claim 10 further having a control valve coupled to the flowline for selectively directing the formation fluid from the flowline into the collection chamber or the wellbore.

13. The apparatus as specified in claim 9 further having a two-way telemetry system for transmitting data between the control circuit and a surface equipment.

14. A modular apparatus for analyzing and collecting formation fluid from a wellbore formation, comprising:
   (a) a probe section having a probe that is adapted to retrieve formation fluid into a flowline;
   (b) a pump section having a pump coupled to the flowline for controlling the formation fluid flow rate into the flowline;
   (c) an acoustic density cell coupled to the pump section and the flowline, the acoustic density cell having an acoustic delay line placed between an acoustic transducer and a first side of the flowline and a receiver placed opposite the transducer on a second side of the flowline, said acoustic transducer being adapted to transmit acoustic signals within a predetermined frequency range and receive acoustic signals; and
   (d) a control circuit coupled to the acoustic density cell for processing acoustic signals received by the transducer and the receiver.

15. A system for analyzing and collecting formation fluid from a wellbore formation, comprising:
   (a) a downhole formation testing tool having
      (I) a probe that is adapted to retrieve formation fluid into a flowline;
      (ii) a pump coupled to the flowline for controlling the formation fluid flow rate into the flowline;
      (iii) an acoustic density cell coupled to the flowline, the acoustic density cell having an acoustic delay line placed between an acoustic transmitter and a first side of the flowline and a receiver placed opposite the transmitter on a second side of the flowline, said acoustic transmitter being adapted to transmit acoustic signals within a predetermined frequency range; and
      (iv) a control circuit coupled to the acoustic density cell for processing acoustic signals received by the receiver so as to generate acoustic data and control signals;

(b) a surface control unit coupled to the downhole tool, said surface control unit having a computer for receiving the processed acoustic signals from the downhole tool and determining the fluid density and fluid compressibility therefrom, said control unit transmitting command signals to the control circuit for controlling the flow rate into the flowline as a function of the fluid density and compressibility measurements so as to maintain the pressure in the flowline above the bubble point pressure of any gas contained in the formation fluid; and (c) a two-way telemetry system for transmitting data between the downhole formation testing tool and the surface control unit.

16. A system for retrieving and collecting a formation fluid from a zone of interest in a wellbore, comprising:

(a) a probe adapted for placement against the zone of interest in the wellbore for receiving the formation fluid;

(b) a pump for controlling the flow rate of the formation fluid from the probe into a flowing used for retrieving said formation fluid;

(c) an acoustic density cell coupled along the flowline for providing signals representative of the speed of sound in the fluid, acoustic impedance and acoustic absorption coefficient of the fluid flowing through the flowline; and (d) a preprogrammed microprocessor for determining the density and compressibility of the formation fluid from the signals representative of speed of sound in the fluid and acoustic absorption coefficient of the fluid and in response thereto controlling the flow of the formation fluid so as to maintain the pressure in the flowline above the bubble point pressure of the fluid.

17. A system for retrieving and collecting a formation fluid from a zone of interest in a wellbore, comprising:

(a) a probe adapted for placement against the zone of interest in the wellbore for receiving the formation fluid;

(b) a pump for controlling the flow rate of the formation fluid from the probe into a flowline used for retrieving said formation fluid;

(c) an acoustic density cell coupled along the flowline for providing signals representative of the speed of sound in the fluid, acoustic impedance and acoustic absorption coefficient of the formation fluid flowing through the flowline;

(d) a control valve for controlling the flow rate of the formation fluid from the flowline into a chamber; and (e) a control unit for causing the flow rate through the pump to change as a function of the fluid density and compressibility of said formation fluid in a manner which ensures that the pressure in the flowline remains above the bubble point pressure of the fluid, said control unit further determining when the fluid in the flowline is substantially free of mud filtrates and causing the valve to discharge such filtrate free fluid into the chamber.

18. The apparatus as specified in claim 17 wherein the control unit contains a computer and a display and monitor.

19. A method for retrieving a formation fluid from a zone of interest in a wellbore, said method comprising the steps of:

(a) withdrawing the formation fluid from the zone of interest into a flowline;

(b) determining the speed of sound in the fluid, acoustic impedance and acoustic absorption coefficient of the fluid flowing through the flowline;

(c) determining the density and compressibility of the fluid from the speed of sound in the fluid, acoustic impedance and the acoustic absorption coefficient of the fluid flowing through the flowline; and (d) controlling the flow of the fluid into the flowline based on the fluid density and the compressibility of the fluid flowing through the flowline so as to ensure that the pressure in the flowline remains above the bubble point of the fluid.

20. A method for determining bubble point pressure of a formation fluid in a wellbore, comprising:

(a) discharging the formation fluid from a zone of interest into a flowline;

(b) determining the speed of sound in the fluid; acoustic impedance and acoustic absorption coefficient of the fluid flowing through the flowline;

(c) determining the density and compressibility of the fluid from the speed of sound in the fluid, acoustic impedance and the acoustic absorption coefficient of the fluid flowing through the flowline;

(d) changing the fluid flow rate into the flowline; and (e) repeating steps (b)–(d) a desired number of times, recording the pressure in the flowline and the compressibility corresponding to each flow rate and determining therefrom the bubble point pressure of the fluid.

21. The method as specified in claim 20 wherein the formation fluid flow rate into the flowline is controlled by a pump by remote means.

22. A method for retrieving and collecting a formation fluid from a zone of interest in a wellbore, said method comprising the steps of:

(a) sealingly placing a probe against the zone of interest in the wellbore;

(b) controllably allowing the fluid from the zone of interest to flow from the probe into a flowline;

(c) determining the density and compressibility of the fluid in the flowline;

(d) determining a condition of the fluid indicative of the pressure in the fluid relative to a bubble point pressure from the density and compressibility of the fluid;

(e) controlling the flow of the fluid into the flowline based on the determination of the fluid condition so as to maintain the fluid in the flowline above the bubble point of any gas contained in the fluid;

(f) discharging the fluid from the flowline into the wellbore until the fluid in the flowline is substantially free from formation mud filtrates, thereby providing substantially clean fluid; and (g) collecting the clean fluid from the flowline into a storage chamber.

23. A method of determining the fluid characteristics downhole, comprising:

(a) transmitting an acoustic signal of known amplitude through a delay line and a fluid at a known time from a first transducer;

(b) receiving and recording the amplitude and arrival time of a resulting echo signal from the interface of the delay line and the fluid;

(c) receiving and recording amplitude and arrival time of the acoustic signal transmitted through the delay line and the fluid by a second transducer; and (d) determining the speed of sound in the fluid, acoustic impedance and the acoustic absorption coefficient of the fluid.

24. An apparatus for determining the speed of sound in a fluid in a flowline and acoustic impedance and the acoustic absorption coefficient of the fluid, comprising:
   (a) a first delay line having a first surface and a second surface wherein the first surface is placed on one side of the fluid flowline;
   (b) a first acoustic transducer having a first surface and a second surface wherein the first surface of the first transducer is bonded to the second surface of the first delay line;
   (c) a first backing having a first surface and a second surface wherein the first surface is bonded to the second surface of the first acoustic transducer;
   (d) a second acoustic delay line having a first surface and a second surface wherein the first surface is placed on the side of the flowline opposite to the first surface of the first delay line on the fluid flowline;
   (e) a second acoustic transducer having a first surface and a second surface wherein the first surface of the first transducer is bonded to the second surface of the second delay line; and
   (f) a second backing having a first surface and a second surface wherein the first surface is bonded to the second surface of the second acoustic transducer.

25. The apparatus as specified in claim 24, wherein:
   (a) the first acoustic transducer or the second acoustic transducer is used as an acoustic transmitter and receiver;
   (b) the remaining of said first and second acoustic transducers is used as an acoustic receiver; and
   (c) the first delay line and second delay line have sufficient thickness such that the arrival times of the acoustic signal transmitted from the transmitter/receiver transducer and resulting echo signal reflected from the delay line surface bonded to the transmitter/receiver transducer are identifiable.

26. The apparatus as specified in claim 25, wherein:
   (a) the first acoustic transducer and the second acoustic transducer are made from a piezoelectric material; and
   (b) the first backing and the second backing are of sufficient thickness such that the acoustic signal reflected from the second surface of the backing does not interfere with the receiver operation of the transmitter/receiver transducer.

* * * * *